United States Patent [19]
Grebow et al.

[11] Patent Number: 5,618,845
[45] Date of Patent: Apr. 8, 1997

[54] ACETAMIDE DERIVATIVE HAVING DEFINED PARTICLE SIZE

[75] Inventors: Peter E. Grebow, Penllyn, Pa.; Vincent Corvari, Hockessin, Del.; David Stong, Coatsville, Pa.

[73] Assignee: Cephalon, Inc., West Chester, Pa.

[21] Appl. No.: 319,124

[22] Filed: Oct. 6, 1994

[51] Int. Cl.$^6$ .............................. A61K 9/14; A61K 31/16
[52] U.S. Cl. ............................................. 514/618; 424/489
[58] Field of Search ............................. 424/489; 514/618

[56] References Cited

U.S. PATENT DOCUMENTS

| | | | |
|---|---|---|---|
| 4,002,718 | 1/1977 | Gardella et al. | 424/37 |
| 4,122,157 | 10/1978 | Huber | 424/21 |
| 4,177,290 | 12/1979 | Lafon | 514/618 |
| 4,196,188 | 4/1980 | Besins | 424/37 |
| 4,332,721 | 6/1982 | Bernini | 260/239.57 |
| 4,713,246 | 12/1987 | Begum et al. | 424/455 |
| 4,880,623 | 11/1989 | Piergiorgio et al. | 424/465 |
| 4,895,726 | 1/1990 | Curtet et al. | 424/456 |
| 4,927,855 | 5/1990 | Lafon | 514/618 |
| 5,021,242 | 6/1991 | Romer et al. | 424/436 |
| 5,180,745 | 1/1993 | Lafon | 514/618 |
| 5,202,129 | 4/1993 | Samejima et al. | 424/489 |
| 5,391,576 | 2/1995 | Lafon | 514/618 |

FOREIGN PATENT DOCUMENTS

| | | |
|---|---|---|
| 233106 | 8/1987 | European Pat. Off. . |
| 0233106 | 8/1987 | European Pat. Off. . |
| 462004 | 12/1991 | European Pat. Off. . |
| 547952 | 6/1993 | European Pat. Off. . |
| 594507 | 4/1994 | European Pat. Off. . |
| 94/21371 | 9/1994 | WIPO . |
| WO94/21371 | 9/1994 | WIPO . |
| 95/1171 | 1/1995 | WIPO . |
| 95/00132 | 1/1995 | WIPO . |
| 85/12944 | 2/1996 | WIPO . |

OTHER PUBLICATIONS

Remington's Pharmaceutical Sciences 16th Ed (1980) pp. 1355–1368, 305–306, 1535–1545.

Shepherd Othero Sclerosis 110/Suppl !555–563(1994) Micronized Lenojitrate.

Kondo Biol. Pharm Bull. 16(8):746–800 (1993) HO–221–A Micronized Poorly Solable Drug.

Carlson et al Clin. Ther. 15(5):788–796 (1993) Micronized Glyburide.

Treffel et al Acta Derm. Venerol. 72(1):65–67 (1992) Micronized 5–Methoxypsoralen.

Hargrove et al AM. J. Abstrt. Gynecol. 161(4):948–951 (1989) Micronized Progesterone.

Stock et al Bor. J. Dermatol. 112(4):469–473 (1985) Micronized 5–Methoxypsoralen McInnes et al. J. Clin Pharmacol 22(8):410–417 Micronized Spironolactone.

Lavharanta et al Arch. Dermatol. Res. 273(1/2) 111–114 (1982) Micronized 8–Methoxypsoralen.

Bastuji H. et al.; "Successful Treatment of Idiopathic Hypersomnia and Narcolepsy with Modafinil"; *Prog. Neuro–Psychopharmacol. & Biol. Psychiat.* 12:695–700 (1988).

Becue T. et al.; "Confirmation of the Structure of By–Products in the Synthesis of Modafinil by Liquid Chromatography–Mass Spectrometry"; *J. Chromatography* 557:489–494 (1991).

Drouin J.E. et al.; "Optimization of the Mobile Phase for the Liquid Chromatographic Separation of Modafinil Optical Isomers on a Chiral–AGP Column"; *J. Chromatography* 605:19–31 (1992).

Duteil J. et al.; "Central $\alpha_1$–Adrenergic Stimulation in Relation to the Behavior Stimulating Effect of Modafinil; Studies with Experimental Animals"; *European J. Pharmacol.* 180:49–58 (1990).

*Drugs of the Future;* "Modafinil"; 15(2):130–132 (1990).

Fuxe K. et al.; "Evidence for a Protective Action of the Vigilance Promoting Drug Modafinil on the MPTP–Induced Degeneration of the Nigrostriatal Dopamine Neurons in . . . "; *Exp. Brain Res.* 88:117–130 (1992).

Lyons T.J. et al.; "Modafinil: The Unique Properties of a New Stimulant"; *Aviation, Space & Environ. Med.* 432–435 (1991).

Milhaud C. et al.; "Effects of Modafinil, An Alpha I Adrenergic Type Psychostimulant on the Sleep of Monkeys"; *Psychopharmacology* 96:Abstract No. 31.05.09 (1988).

Milhaud C.L. et al.; "Presentation of d'un Nouveau Stimulant:Le CRL–40476"; *AGARD Conf. Proc.* 415:5–1–5–7 (1987).

Moachon G. et al.; "Simultaneous Determination of Modafinil and its Acid Metabolite by High–Performance Liquid Chromatography in Human Plasma"; *J. Chromatography B* 654:91–96 (1994).

Roze C. et al.; "Drug CRL 40 028–Induced Inhibition of Pancreatic Secretion in Rats"; *Arch Int Pharmacodyn* 265:119–127 (1983).

Saletu B. et al.; "Differential Effects of a New Central Adrenergic Agonist–Modafinil–and D–Amphetamine on Sleep and Early Morning Behaviour in Young Healthy Volunteers"; *Int J Clin Pharm Res* IX(3):183–195 (1989).

*Primary Examiner*—Shep K. Rose
*Attorney, Agent, or Firm*—Fish & Richardson P.C.

[57] ABSTRACT

Pharmaceutical compositions comprising modafinil in the form of particles of defined size. The particle size of modafinil can have a significant effect on the potency and safety profile of the drug.

6 Claims, 7 Drawing Sheets

ACETAMIDE DERIVATIVE HAVING DEFINED PARTICLE SIZE

BACKGROUND OF THE INVENTION

Publications cited in this document are incorporated herein by reference.

This invention relates to the acetamide derivative modafinil. Modafinil ($C_{15}H_{15}NO_2S$), is 2-(benzhydrylsulfinyl)acetamide, and is also known as 2-[(diphenylmethyl)sulfinyl] acetamide.

Modafinil has been described as presenting a "neuropsychopharmacological spectrum characterized by the presence of excitation with hyperactivity and of hypermotility; and by the absence of stereotypy (except in high doses) and of potentialisation of the effects of apomorphine and amphetamine" (U.S. Pat. No. 4,177,290; hereinafter the "'290 patent," which is incorporated herein by reference). A single administration of modafinil results in increased locomotor activity in mice and increased nocturnal activity in monkeys (Duteil et al., *Eur. J. Pharmacol.* 180:49 (1990)). The neuropsychopharmacological profile of modafinil has been distinguished from that of amphetamines (Saletu et al., *Int. J. Clin. Pharm. Res.* 9:183 (1989)). Modafinil is thought to modulate the central postsynaptic $alpha_1$-adrenergic receptor, without participation of the dopaminergic system (Duteil et al., supra). Modafinil has been successfully tested in humans for treatment of idiopathic hypersomnia and narcolepsy (Bastuji et al., *Prog. Neuro-Psych. Biol. Psych.* 12:695 (1988)).

Narcolepsy is a chronic disorder characterized by intermittent sleep attacks, persistent, excessive daytime sleepiness and abnormal rapid eye movement ("REM") sleep manifestations, such as sleep-onset REM periods, cataplexy, sleep paralysis and hypnagogic hallucinations, or both (Assoc. of Sleep Disorders Centers, *Sleep* 2:1 (1979)). Most patients with narcolepsy also have disrupted nocturnal sleep (Montplaisir, in Guilleminault et al. eds., *Narcolepsy*, Spectrum Pub., New York, pp. 43–56). Pathological somnolence, whether due to narcolepsy or other causes, is disabling and potentially dangerous. Causes of pathological somnolence, other than narcolepsy, include chronic sleep loss (Carskadon et al., *Sleep*, 5:S73 (1982); Carskadon et al., *Psychophysiology*, 18:107 (1981)); sleep apnea (Kryger et al., *Principles and Practice of Sleep Medicine*, W. B. Saunders Co., Philadelphia, Pa. (1989)); and other sleep disorders (*International Classification of Sleep Disorders: Diagnostic and Coding Manual*, American Sleep Disorder Association, Rochester, Minn. (1990)). Whether due to narcolepsy or other causes, pathological somnolence produces episodes of unintended sleep, reduced attention, and performance errors. Consequently, it is linked to a variety of transportation and industrial accidents (Mitler et al., *Sleep* 11:100 (1988)). A therapeutic agent that reduces or eliminates pathological somnolence would have important implications not only for individual patients, but also for public health and safety.

Other uses of modafinil have been presented. U.S. Pat. No. 5,180,745 discloses the use of modafinil for providing a neuroprotective effect in humans, and in particular for the treatment of Parkinson's disease. The levorotatory form of modafinil, i.e., (−)benzhydrylsulfinyl-acetamide, may have potential benefit for treatment of depression, hypersomnia and Alzheimer's disease (U.S. Pat. No. 4,927,855). European Published Application 547952 (published Jun. 23, 1993) discloses the use of modafinil as an anti-ischemic agent. European Published Application 594507 (published Apr. 27, 1994) discloses the use of modafinil to treat urinary incontinence.

SUMMARY OF THE INVENTION

Our invention discloses a pharmaceutical composition comprising modafinil in the form of particles of a defined size, and the use of such composition. We have discovered that the size of modafinil particles is important to the potency and safety profile of the drug.

"Particle," as used herein, refers to an aggregated physical unit of the acetamide compound, i.e., a piece or a grain of acetamide. For example, FIGS. 2–5 provide photographic representations of various modafinil particles from Lots E-D and L-1.

As used herein, the term "mean," when used in reference to the size of modafinil particles, refers to the sum of the size measurements of all measurable particles measured divided by the total number of particles measured. For example, for five measurable particles which could be measured, and were determined to have diameters of 20 microns, 23 microns, 20 microns, 35 microns and 20 microns, the mean diameter would be 23.6 microns. As used herein, the term "diameter" is a volumetric measurement based on the presumed spherical shape of modafinil particles.

As used herein, the term "median," when used in reference to the size of modafinil particles, indicates that about 50% of all measurable particles measured have a particle size less than the defined median particle size value, and that about 50% of all measurable particles measured have a particle size greater than the defined median particle size value. For example, for the five particle values listed above, the median diameter would be 20 microns.

As used herein, the term "mode," when used in reference to the size of modafinil particles, indicates the most frequently-occurring particle size value. For example, for the five particle values listed above, the mode diameter would be 20 microns.

As used herein, the term "percent cumulative," when used in reference to the size of modafinil particles, refers to an aggregate of the individual percent values for all measurable particles measured at specified diameters.

As used herein, "about" means plus or minus approximately ten percent of the indicated value, such that "about 20 microns" indicates approximately 18 to 22 microns. The size of the particle can be determined, e.g., by the methods provided below, and by conventional methods known to those of skill in the art.

In accordance with the invention disclosed herein, the mean particle size for a modafinil particle preferably ranges from about 2 microns to about 19 microns, more preferably from about 5 microns to about 18 microns, and most preferably from about 10 microns to about 17 microns.

In accordance with the invention disclosed herein, the median particle size for modafinil preferably ranges from about 2 microns to about 60 microns, more preferably from about 10 microns to 50 microns, and most preferably from about 20 microns to about 40 microns.

In accordance with the invention disclosed herein, the mode particle size for modafinil preferably ranges from about 2 microns to about 60 microns, more preferably from about 10 microns to about 50 microns, and most preferably from about 20 microns to about 40 microns.

We view the median measurement as having greater importance compared to the mode or mean values in that the median value provides an indication of the distribution of the particles measured in a given population. While not necessarily a limitation but rather an indicator of the consistency of the population measured, the ratio of median: mean: mode would ideally be 1:1:1; however, a ratio of median to mean of 1:2.50 to 1:0.50 is acceptable, and a ratio of median to mode of 1:2.50 to 1:0.50 is acceptable. Ideally, the standard deviation between the mean, median and mode measurements of a modafinil population would approach zero, indicating that every particle in the population measured was substantially identical or met the criteria for an ideal, normalized distribution. A standard deviation of less than about 25 between the mean, median and mode measurements is acceptable as an indication of the consistency of the population of the particles measured.

In accordance with the invention disclosed herein, it is preferable that not more than about 5% of the cumulative total (percent cumulative) of modafinil particles in any one dose provided to a mammal have particle sizes greater than about 200 microns; it is more preferable that not more than about 5% of the cumulative total (percent cumulative) of modafinil particles in any one dose provided to a mammal have particle sizes greater than about 190 microns; it is most preferable that not more than about 5% of the cumulative total (percent cumulative) of modafinil particles in any one dose provided to a mammal have particle sizes greater than about 180 microns. Thus, a "substantially homogeneous mixture" of modafinil particles, as utilized herein, refers to a mixture of modafinil particles in which at least about 95% of the particles in that mixture are less than a defined size.

The value ranges defined above are based upon measurements made utilizing technology and instruments developed by the Hiac/Royko Division of Pacific Scientific (11801 Tech Road, Silver Spring, Md. 20904, United States of America). As those in the art may appreciate, different instruments manufactured by different companies may provide different measurements for the same particles. For example, in a characteristic modafinil lot (Lot L-2), the mean, median, and mode particle measurements obtained using a Coulter Counter TA II sizing counter were 43, 31, and 29 microns, respectively. Using a Hiac/Royko Model 9064 sizing counter, the mean, median and mode particle measurements obtained for Lot L-2 were 18.75, 31.41 and 25.31 microns, respectively. These differences are presumably predicated upon the different approaches used in measuring particles of such diminutive sizes. Thus, the value ranges provided above are relative and are most preferably to be considered in view of utilization of instruments and operating systems manufactured by Hiac/Royko, for example, and preferably, the Hiac/Royko Model 9064 system sizing counter.

Modafinil particles of the invention can be in the form of a pharmacologically acceptable salt, e.g., an acidic or basic addition salt.

In another aspect, the invention features a method of altering a somnolent state, e.g., narcolepsy, idiopathic hypersomnia and related sleep disorders, using modafinil particles of a defined size. The method involves administering to a mammal a pharmaceutical composition comprising an effective amount of modafinil in the form of particles of a defined size.

"An effective amount", as used herein, is an amount of the pharmaceutical composition that is effective for treating a somnolent or somnolescent state, i.e., an amount of modafinil of a defined particle size that is able to reduce or eliminate the symptoms of a somnolescent state. An effective amount of a pharmaceutical composition of the invention is useful for enhancing alertness, or increasing regularity of sleep rhythms.

A "pharmaceutical composition", as used herein, means a medicament for use in treating a mammal that comprises modafinil of a defined particle size prepared in a manner that is appropriate for administration to a mammal. A pharmaceutical composition according to the invention may also, but does not of necessity, include a non-toxic pharmaceutically acceptable carrier.

The pharmaceutical composition of the invention can contain at least about 50 mg, preferably at least about 100 mg, or more preferably at least about 200 mg of modafinil having a particle size as defined above. The pharmaceutical composition preferably contains no more than about 700 mg; more preferably, no more than about 600 mg; and most preferably, no more than about 400 mg, of modafinil having a particle size as defined above.

Other features and advantages of the invention will be apparent from the following detailed description and from the claims.

DETAILED DESCRIPTION

We first briefly describe the drawings.

I. Drawings

II. The Invention

The invention results from our discovery that the particle size, and the consistency of the particle size, of modafinil can have a significant effect on its potency and safety profile.

The first human trials for the use of modafinil to treat narcolepsy took place outside of the United States of America. The modafinil used in the initial studies was prepared in non-commercial scale lots (referred to herein as "early" or "E" lots). Pursuant to our discovery of the present invention, it was observed that the early lots had a median particle size of between 80 microns ("μm") and 150 μm. In the initial safety studies conducted outside of the United States, early lot modafinil was administered to humans without reports of clinically significant adverse events in acute administration.

Separate safety and efficacy studies of modafinil were subsequently conducted in the United States under the direction of Cephalon, Inc. using modafinil lots prepared by a method scaled up for commercial production (referred to herein as "late" or "L" lots). When the late lots of modafinil were administered to humans in the United States, the initial clinical trial revealed the occurrence of unanticipated adverse events at a dose level (800 mg/day) previously determined to be acceptable during studies conducted outside of the United States. We discovered that the late lots had a median particle size of between 30 and 50 μm. Thus, the initial human trials conducted in the United States were performed with modafinil having a significantly smaller particle size.

As was subsequently discovered, lots comprising a smaller particle size resulted in an increase in the potency of modafinil, leading us to conclude that the drug can be more readily absorbed when compared to modafinil derived from lots comprising a larger particle size. Therefore, modafinil particles of a defined size provide at least two significant and unexpected advantages. First, potency is increased. A smaller average particle size allows achievement of a given modafinil plasma concentration at a lower oral dose. Second, with the knowledge of the importance of particle size on potency, the safety profile of the drug can be more accurately controlled because dosing with consistent and defined particle sizes allows for greater reliability in the dosing of the drug necessary to achieve a desired result.

III. Human Clinical Safety Studies—Foreign

The safety and pharmacodynamics of modafinil were initially characterized in several studies conducted outside the United States using modafinil obtained from the early lots. During these studies, modafinil in amounts of up to 4,500 mg have been ingested without the occurrence of significant clinical side effects (see, for example, Bastuji, supra; see also Lyons, T. J. and French, J. *Aviation, Space and Environmental Medicine* May, 1991, 432). No statistically or clinically significant hemodynamic changes in heart rate or blood pressure in patients or in healthy volunteers using modafinil doses tested in the foreign studies have been reported.

IV. Human Clinical Safety Studies—United States

While significant testing of modafinil had already been conducted outside the United States, new drug candidates, such as modafinil, typically undergo clinical research in the United States in order to corroborate the information obtained in foreign studies. The first United States clinical evaluation of modafinil was a double-blind, ascending dose study involving oral administration of modafinil to healthy males (i.e., physically and mentally healthy male subjects 18 to 50 years of age; average body weight of −10% to +15% of normal weight for age, height, frame and sex; 2101).

The planned doses for the first United States clinical trial were 200, 400, 600, 800, 1000, 1200 and 1400 mg/day of modafinil or placebo. These dose levels were based upon the safety profile observed during the foreign clinical testing of modafinil. Subsequent doses were given only when it was determined that the previously administered dose was safe and well tolerated. For example, the safety data for the 200 mg study dose was reviewed and assessed before other volunteers received the 400 mg dose.

In this first United States Phase I clinical study, modafinil from Lot L-1 was utilized. Complete data were obtained for three of the seven modafinil dose levels intended for testing, i.e., 200, 400, and 600 mg/day. However, elevations in heart rate and blood pressure were noted in two of the volunteers at the 800 mg dose level. These symptoms resolved without treatment or sequelae following drug discontinuation. This was surprising and completely unexpected, given the escalation of modafinil dosing observed in the foreign studies. Because these results were unexpected and because they occurred in healthy volunteers, these adverse events led to discontinuation of dosage progression at the 1000, 1200 and 1400 mg/day levels until the cause of such results was determined.

V. Discrepancy Between the Foreign and United States Results

In searching for the cause of the discrepancy, we compared plasma levels of modafinil measured in the first United States study and the preceding foreign studies. We found that at a given oral dose, when compared to subjects in the foreign studies, subjects in the United States study had higher peak modafinil plasma levels.

The modafinil tablets used in the foreign studies were based upon early lots of modafinil, while the modafinil tablets used in the United States study were based upon late lots of modafinil. We theorized that a difference in bioavailability of the different lots of modafinil was responsible for the differences in maximum tolerable dose observed in the foreign and United States clinical studies. Although not obvious or readily apparent, one of several possible explanations which we posited was a possible difference in the modafinil particle size used in the foreign and the United States studies.

VI. Particle Size Analysis

Following this assumption, we compared various parameters from lots of the bulk drug; such comparisons had not been conducted previously, given the assumption that the modafinil being tested in the United States was the "same" as that investigated outside of the United States. Particle size distribution of the bulk drug was among the parameters examined. We have performed modafinil particle size analyses with a Hiac/Royko Model 9064 sizing counter, a Coulter Counter sizing counter, by optical microscopy and by scanning electron microscopy.

Our particle size measurements were obtained using a Hiac/Royco Model 9064 sizing counter following manufacturer instructions (400 μm aperture; saturated water with modafinil solution; PDAS program). A summary of the results of these measurements is presented in Table 1, which includes the mean, median and mode particle sizes for six representative lots of modafinil. For comparative purposes, the standard deviation values derived from the mean, median and mode measurements are provided, as are the ratio values of median:mean:mode. Lots E-A, E-B, E-C and E-D were among the so-called early lots, and Lots L-1 and L-2 were among the so-called late lots.

TABLE 1

MODAFINIL PARTICLE DIAMETER

| LOT | MEAN* (μm) | MEDIAN* (μm) | MODE* (μm) | STD DEVIATION BETWEEN MEAN, MEDIAN, MODE | MEDIAN:MEAN:MODE |
|---|---|---|---|---|---|
| E-A | 34.60 +/− 5.21 | 143.65 +/− 3.26 | 176.48 +/− 5.32 | 74.27 | 1:4.15:.81 |
| E-B | 29.99 +/− 1.09 | 89.10 +/− 4.28 | 78.59 +/− 2.60 | 31.53 | 1:2.97:1.13 |
| E-C | 28.27 +/− 4.10 | 79.00 +/− 3.78 | 101.00 +/− 40.92 | 37.30 | 1:2.79:.78 |
| E-D | 22.14 +/− 0.76 | 94.05 +/− 13.75 | 158.63 +/− 63.81 | 68.28 | 1:4.25:.59 |
| L-1 | 21.40 +/− 2.52 | 50.18 +/− 12.57 | 56.56 +/− 22.39 | 18.73 | 1:2.34:.89 |
| L-2 | 18.75 +/− 1.89 | 31.41 +/− 3.57 | 25.31 +/− 1.34 | 6.36 | 1:1.68:1.24 |

*n = 4; +/− values are standard deviations

Figure 1:
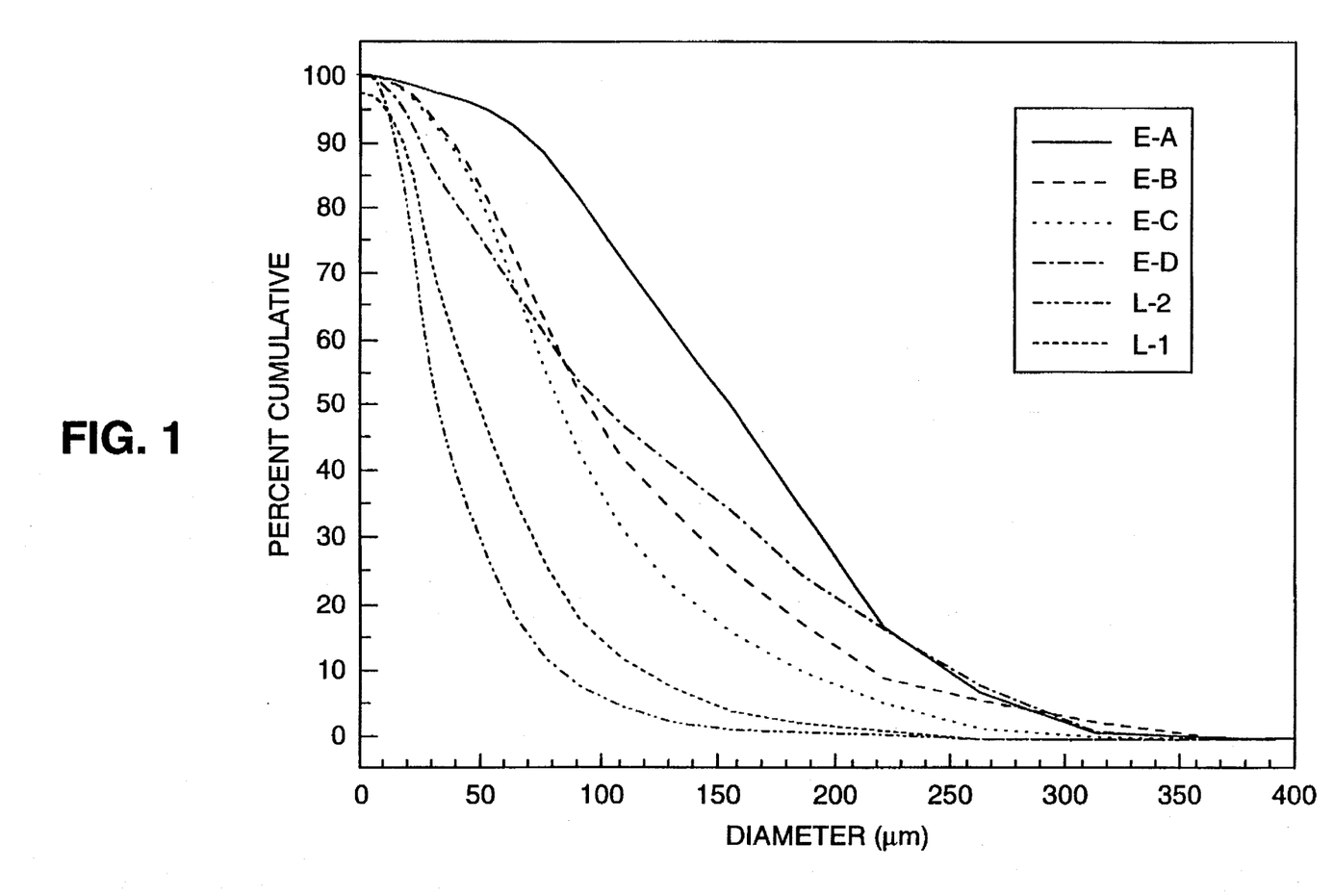
FIG. 1 is a graph depicting particle size distributions for six lots of modafinil: Lots L-1, L-2, E-A, E-B, E-C and E-D.

FIG. 1 is a graph of particle diameter versus percent cumulative particles for late Lots L-1, L-2, and for the early Lots E-A, E-B, E-C, and E-D. The 50 percent cumulative particle size for Lots L-1 and L-2 was between approximately 30 μm and approximately 50 μm, while the 50 percent cumulative particle size for Lots E-A, E-B, E-C, and E-D was between approximately 80 μm and approximately 140 μm.

Figure 2:
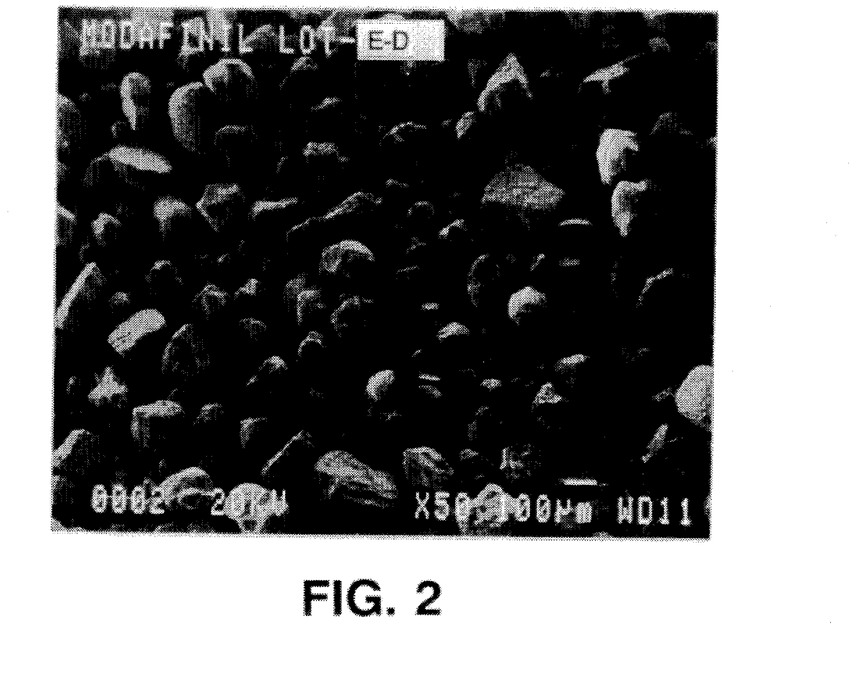
FIG. 2 is a scanning electron micrograph of a sample of modafinil Lot E-D at 50× magnification.
Figure 3:
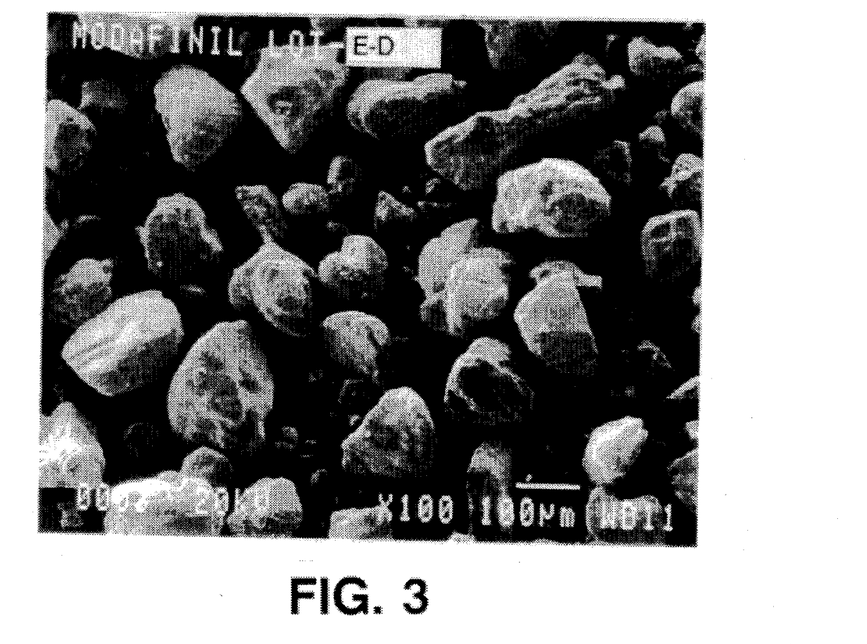
FIG. 3 is a scanning electron micrograph of a sample of modafinil Lot E-D at 100× magnification.
Figure 4:
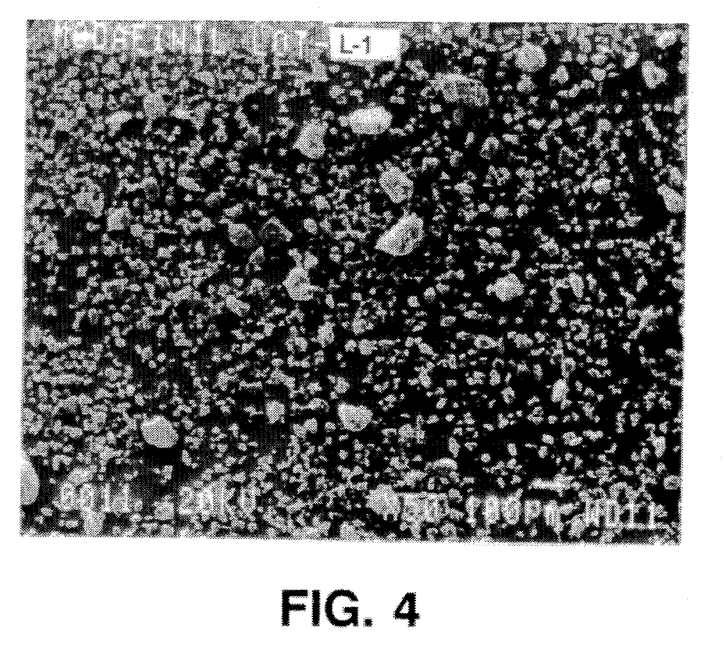
FIG. 4 is a scanning electron micrograph of a sample of modafinil Lot L-1 at 50× magnification.
Figure 5:
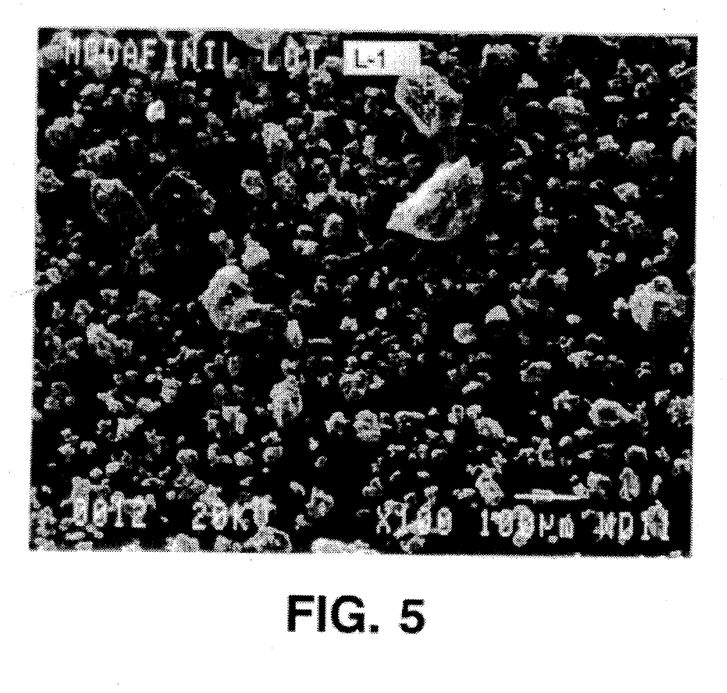
FIG. 5 is a scanning electron micrograph of a sample of modafinil Lot L-1 at 100× magnification.

In addition to the Hiac/Royko data, electron microscopy and optical microscopy were used to verify modafinil particle size and morphology. Representative scanning electron micrographs of early Lot E-D are shown in FIG. 2 (50× magnification) and in FIG. 3 (100× magnification). Representative scanning electron micrographs of late Lot L-1 are shown in FIG. 4 (50× magnification) and FIG. 5 (100× magnification).

It is noted that the size of modafinil particles may be determined by any of several conventional methods. Methods useful for analyzing particle size within the range of 100 Angstroms to 100 μm, include, but are not limited to: laser diffraction particle size analysis, mechanical sieving, optical microscopy, ultracentrifugation, sedimentation, air permeability, electron microscopy, scanning electron microscopy and Coulter Counter techniques. For a general review of methods for determining particle size, see Martin et al., *Physical Pharmacy*, 3rd Ed., Lea & Febiger, Philadelphia (1983). See also O'Conner in *Remington's, infra.*, Section IX.

Optical microscopy is useful for particle size measurement in the range of 0.2 μm to 100 μm. For optical microscopy, an emulsion or suspension, diluted or undiluted, is mounted on a slide or ruled cell. The microscope eyepiece is fitted with a micrometer by which the size of the particles may be estimated.

Mechanical sieving uses a series of standard sieves calibrated by the National Bureau of Standards. Mechanical sieves may be used for screening material as fine as 44 μm (No. 325 sieve). Sieves manufactured by photo-etching and electroforming are available with apertures from 90 μm to 5 μm.

Measurements obtained using instruments and techniques developed by Hiac/Royko are preferred. A Hiac/Royco sizing counter utilizes the principle of light-extinction (obscuration) for particle size detection. The principle involved is that when a particle suspended in a liquid passes through a sensor microcell where a laser beam is directed through a window at the cell, the particles in the fluid block the laser beam from a light-extinction photodiode (photodetector) resulting in a loss of light intensity. This loss of light intensity detected by the photodetector produces an electrical pulse for each particle. These pulses are proportional in amplitude to the light intensity (light extinction) which is a measure of particle size.

VII. Effect of Modafinil Particle Size on Rate of Modafinil Dissolution

Figure 6:
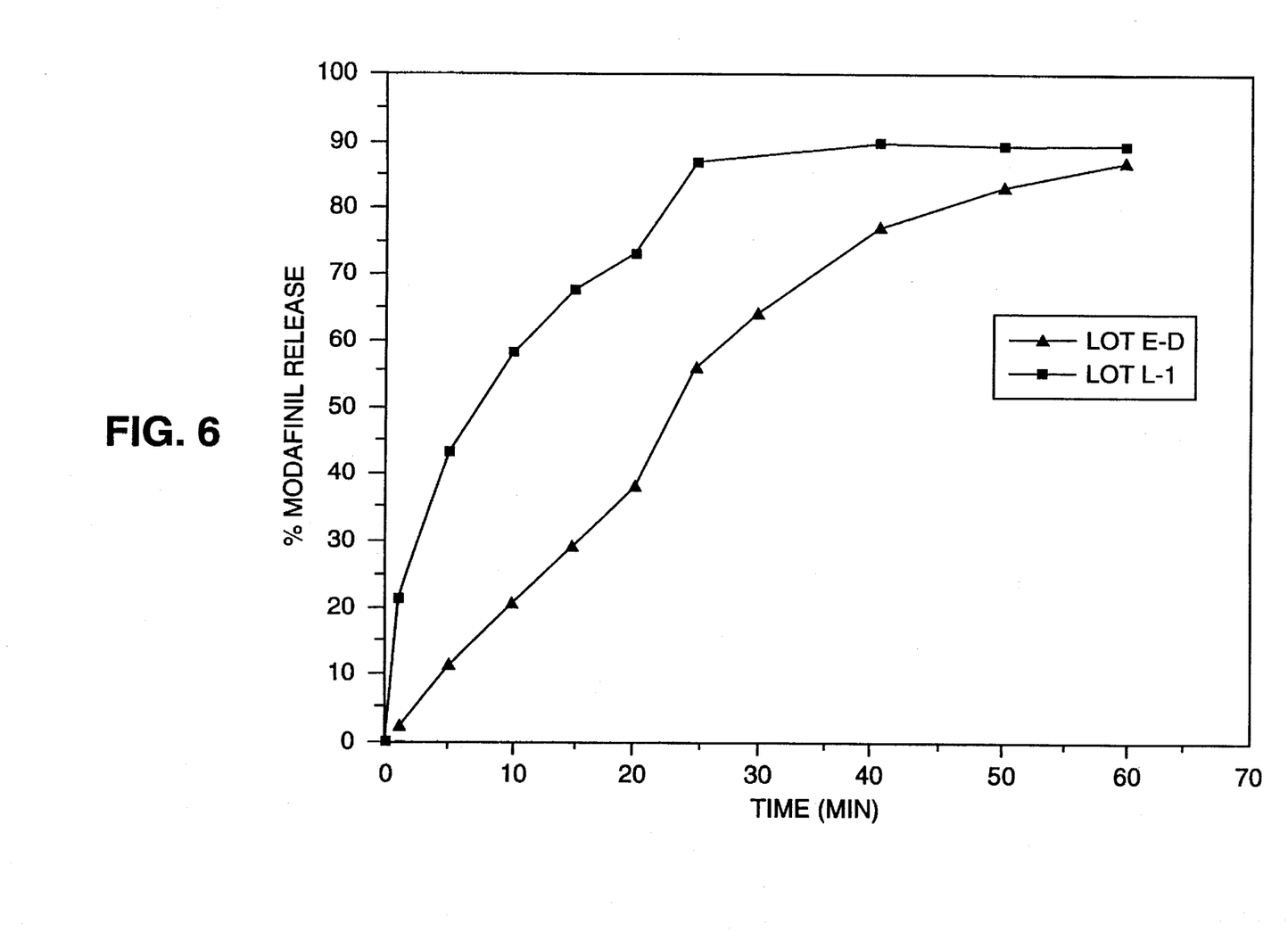
FIG. 6 is a graph depicting the dissolution rate of modafinil particles from Lot E-D (median particle size 94.05 μm) and Lot L-1 (median particle size 50.18 μm).
Figure 7:
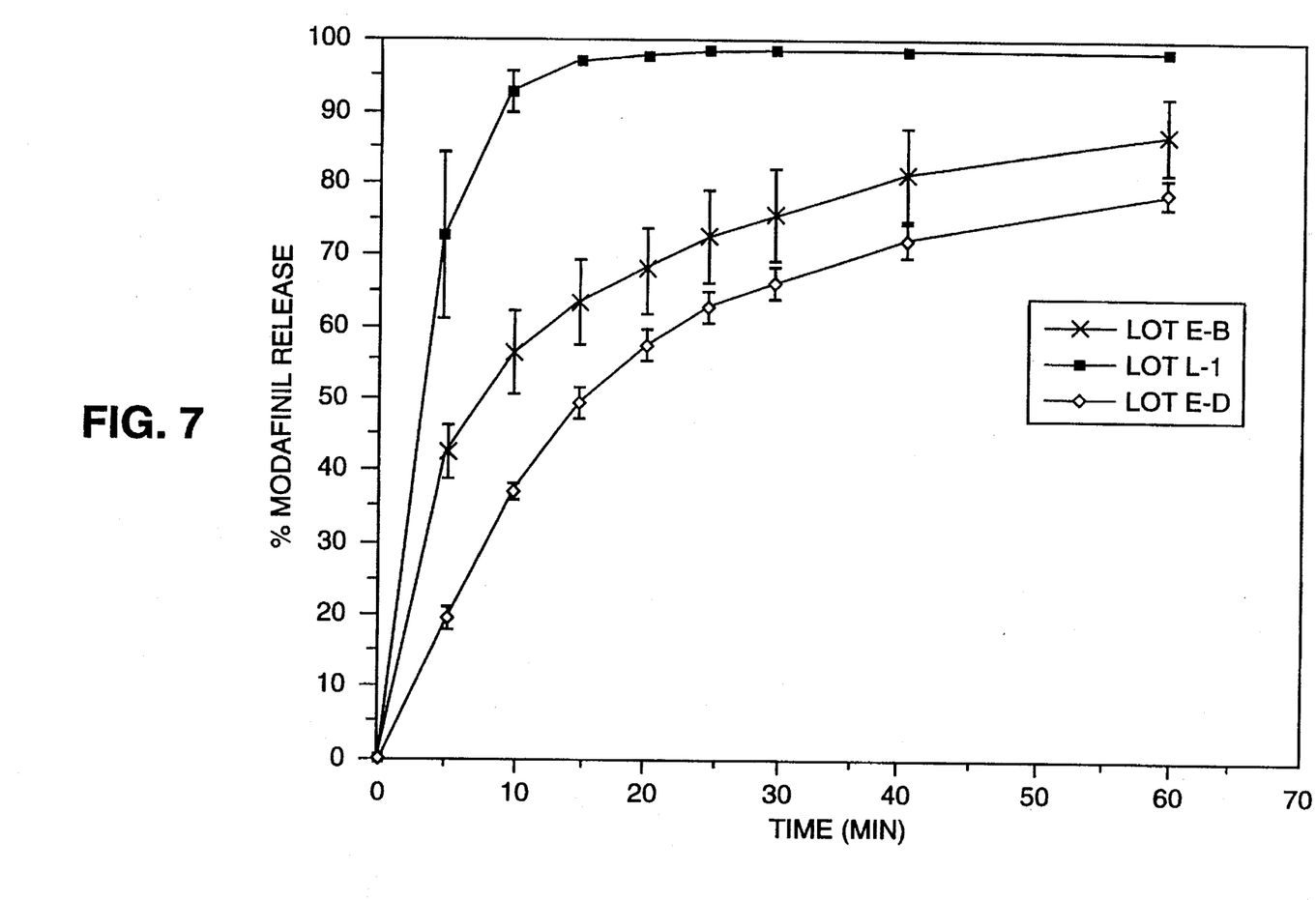
FIG. 7 is a graph depicting the dissolution rate of modafinil particles from Lot E-B (median particle size 89.10 μm), Lot E-D (median particle size 94.05 μm) and Lot L-1 (median particle size 50.18 μm).

We investigated the effect of modafinil particle size on the rate of dissolution. The results of those experiments are summarized in FIG. 6 and FIG. 7.

In the first experiment, 500 ml of deionized water was put in a 1-liter beaker and 50 mg of E-D or L-1 was added. The suspension was stirred constantly with a 5 cm Teflon-coated magnetic stir bar and a magnetic stir plate (Thermolyne model #546725). Samples of 1 ml each were taken at times 0, 1, 5, 10, 15, 20, 25, 30, 40, 50, and 60 minutes, with each sample being replaced with 1 ml of deionized water. The stir plate speed setting was "2" for the first 20 minutes, and "7" from 20 to 60 minutes. Each sample was immediately filtered through a 0.45 μm filter, to remove undissolved particles. The filtered samples were assayed for modafinil, by high performance liquid chromatography, based upon the method of Moachon et al. (*J. Chromatag. B* 654:91 (1994)). Modafinil Lot L-1 (median: 50.18 μm) had a faster dissolution rate than did modafinil Lot E-D (mean: 94.05 μm). The results of the first experiment are summarized in FIG. 6.

A second dissolution rate experiment was conducted to determine relative dissolution rates of modafinil from the capsules used in the dog study (described below) of plasma modafinil levels following oral administration of modafinil from Lots E-B, E-D and L-1. In the second dissolution rate experiment, the solvent was 900 ml of 0.01N HCl, maintained at 37° C. Each sample placed into the solvent consisted of 200 mg of modafinil packed in a gelatin capsule. Stainless steel coils were attached to the capsules to prevent them from floating. A stirring paddle was used at 100 rpm. Solution samples were taken at 0, 5, 10, 15, 20, 25, 30, 40 and 60 minutes. The results of the modafinil capsule dissolution experiment are summarized in FIG. 7.

VIII. Effect of Modafinil Particle Size on Modafinil Plasma Concentration

Given the disparity in results between the foreign and United States studies using what was presumed to be "identical" modafinil, additional non-human analyses were necessary prior to continuation of human clinical trials. Accordingly, animal studies in dogs were carried out to determine the in vivo pharmacokinetics of modafinil with different average particle size diameters, roughly designated as having "small" (Lot L-1) and "large" (Lots E-B and E-D) median particle sizes. Nine male dogs were randomly assigned, according to body weight to three dose groups. Each group was given a single oral dose of 200 of mg modafinil weekly for three weeks in a randomized, crossover design, as described in Table 2.

TABLE 2

| GROUP | NUMBER OF DOGS | WEEK | BULK DRUG LOT AND MEDIAN PARTICLE SIZE |
|---|---|---|---|
| 1 | 3 | 1 | E-D (94.05 μm) |
|   |   | 2 | L-1 (50.18 μm) |
|   |   | 3 | E-B (89.10 μm) |
| 2 | 3 | 1 | L-1 (50.18 μm) |
|   |   | 2 | E-B (89.10 μm) |
|   |   | 3 | E-D (94.05 μm) |
| 3 | 3 | 1 | E-B (89.10 μm) |
|   |   | 2 | E-D (94.05 μm) |
|   |   | 3 | L-1 (50.18 μm) |

After each weekly dose, blood samples (2 ml) were drawn from all animals by venepuncture predose (within one hour of dosing), and at 0.5, 1, 2, 3, 4, 6, 8, 10, 12, 18, 24, and 36 hours post-dose. Blood samples were collected in heparinized (lithium heparin) test tubes and centrifuged at 2,500 to 3,000 rpm. The plasma was drawn off with a glass pipette, and stored frozen (−20° C.) until analyzed. The plasma concentration of modafinil, and its acid and sulfone metabolites were simultaneously determined by high-pressure liquid chromatography, according to the method of Moachon et al. (*J. Chromatag. B* 654:91 (1994)).

Figure 8:
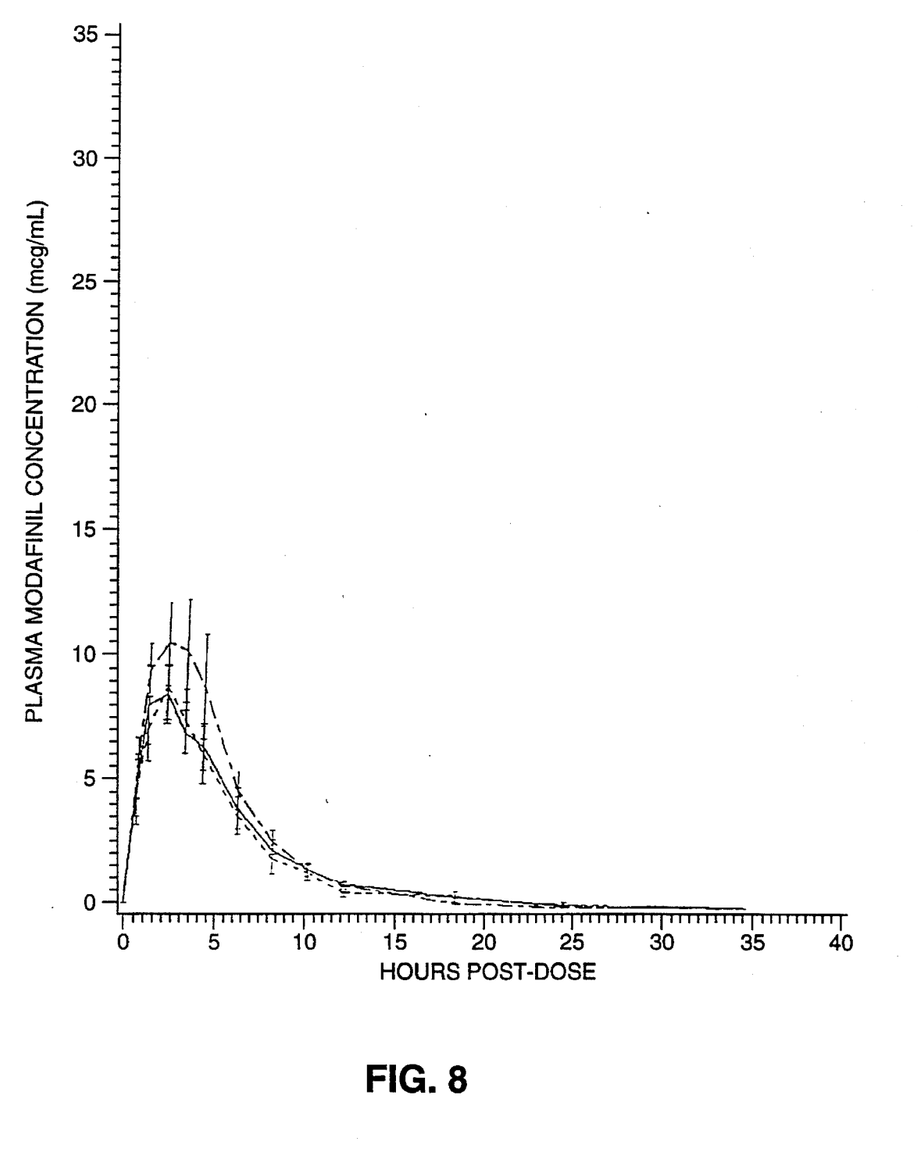
FIG. 8 is a graph depicting mean plasma concentration of modafinil in dogs following single oral doses of modafinil from lots with different particle sizes.
Figure 9:
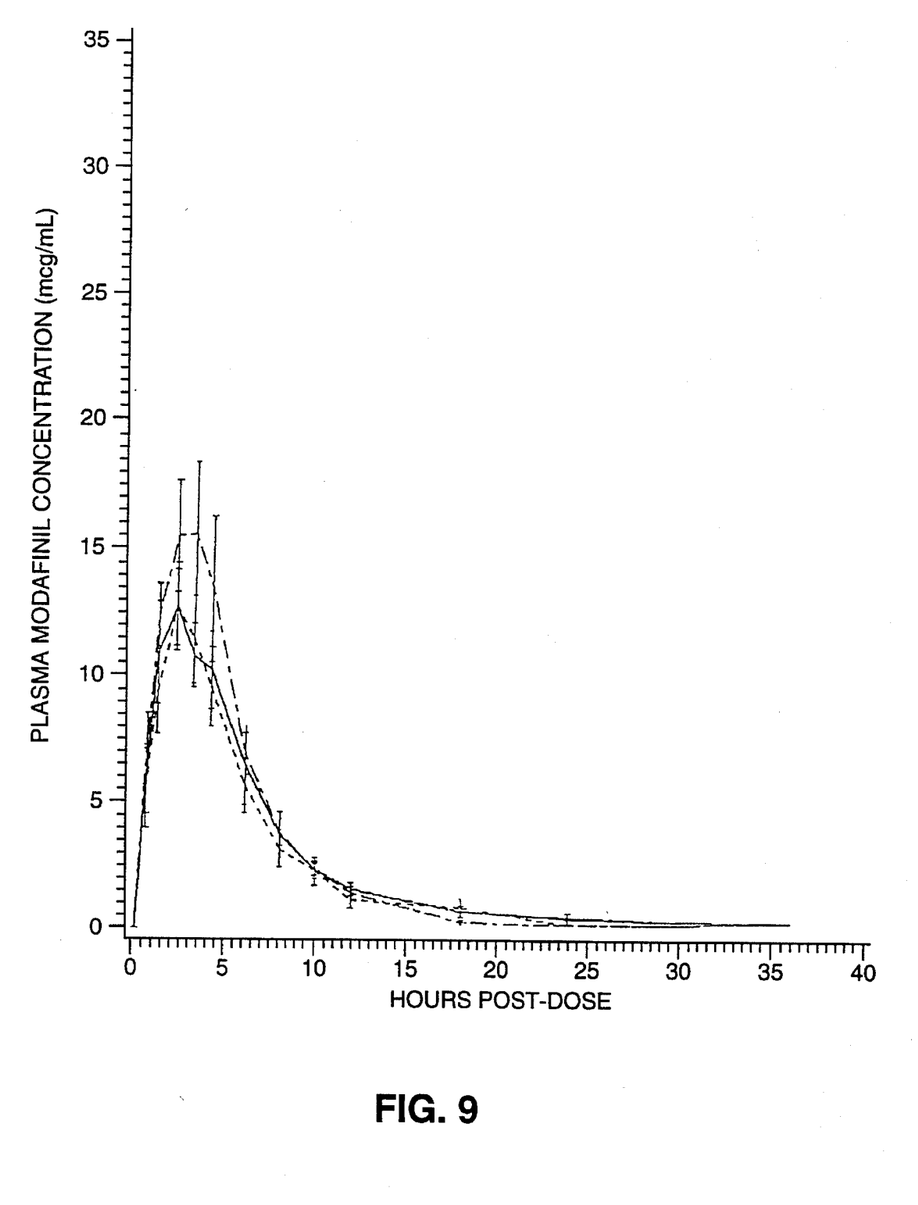
FIG. 9 is a graph depicting mean plasma concentration of modafinil equivalents, i.e., modafinil and modafinil acid metabolite, in dogs, following single oral doses of modafinil from lots with different particle sizes.

Mean plasma modafinil levels in the nine dogs, at 0 to 36 hours after modafinil administration, are depicted in FIG. 8. With "small" particles (Lot L-1), the plasma modafinil concentration peaked at 10 μg/ml. In contrast, with "larger" particles (Lots E-D or E-B), the plasma modafinil concentration peaked at 8 μg/ml. Thus, the modafinil having a median particle size of 50.18 μm resulted in a higher peak plasma concentration than that obtained with the same dose of modafinil administered in the form of larger particles. Similar results were observed regarding the acid metabolite of modafinil, 2-benzhydrylsulfinylacetic acid as depicted in FIG. 9.

These results implicated the consequences of different particle sizes and the importance of controlling modafinil particle size. By controlling the particle size, safety concerns can be addressed. For example, a non-homogenous mixture of modafinil particle sizes may not provide consistent potency nor avoid undesired fluctuations in plasma modafinil concentrations; such fluctuations can lead to undesired and unexpected events. Moreover, the use of modafinil particles having a defined size is more efficient because a given plasma modafinil concentration can be achieved at a lower oral dose.

After the discrepancy between the foreign and first United States studies was resolved and determined to be related to the differences in particle sizes, a second Phase I study was conducted in the United States, to further determine the clinical safety, tolerance and pharmacokinetic properties of modafinil having a particle size as defined. The second study involved normal young males and an experimental design similar to the first United States study (described above). In the second study, all subjects began at 200 mg/day using modafinil from Lots L-1 or L-2. Dosage was then titrated, in 200 mg/day increments, up to the target dose. The results of this study suggested that 600 mg/day was the maximum tolerable dose ("MTD") of modafinil, with 800 mg/day being the minimum intolerable dose.

IX. Methods of Preparing Modafinil Having Defined Size

Modafinil and modafinil-related compounds can be prepared by conventional methods. Methods for preparing modafinil and modafinil-related compounds appears in the '290 patent. Modafinil of the particle size defined herein may be obtained by a variety of approaches utilizing conventional methods, e.g., the methods disclosed in the '290 patent, and then subjecting the modafinil of undefined particle size to conventional methods of milling and sieving. Methods for comminution (i.e., the mechanical process of reducing the size of particles or aggregates) are known to those in the art. Examples are provided in O'Conner et al. Chpt. 88, *Remington's Pharmaceutical Sciences*, 18th Edition, Mack Publishing Co., Easton, Pa. (1990). Following comminution, the particles can be separated into a series of sieve cuts by passing the particles downward through an agitated vertical stack of sieves of decreasing mesh sizes and collecting the granules retained on each sieve or in the bottom pan. Particles which fall outside of a desired range can again be subjected to milling and sieving.

X. Formulation and Administration

An appropriate dosage for modafinil having a defined particle size is between about 50 mg and about 700 mg of modafinil.

The pharmaceutical composition described herein is most preferably administered orally in the form of a vehicle such as a tablet, capsule, powder, pill, liquid/suspension or emulsion. The administration vehicle may comprise a pharmaceutically-acceptable carrier. The carrier may comprise agents that aid solubility, absorption, flavor, color or texture of the vehicle or its contents. Topical administration via an epidermal patch or the like, or administration via direct injection of the drug, is also acceptable.

A vehicle of the invention can include ±10–15% of the modafinil particle, due to factors such as vehicle manufacturing tolerances and expected shelf life of the modafinil. For example, a vehicle labeled as containing 50 mg can be initially prepared with, e.g., 55 or 58 mg of modafinil, with the expectation that after one month to two years of storage, the active amount of modafinil therein has decreased. Vehicles prepared with such adjustments in order to compensate for the expected degradation of the drug fall within the scope of the invention.

While the invention has been described in considerable detail, the invention disclosed herein is not to be limited to the actual description, but is to be afforded the full scope of the appended claims and all equivalents thereto. Although the specific examples presented herein are directed to the use of modafinil of a defined particle size in the mediation of narcolepsy, other uses of modafinil (e.g., for treatment of Parkinson's disease, urinary incontinence, Alzheimer's disorder, etc.) have been presented in the art, and those utilities are appropriate in conjunction with the invention as disclosed herein.

What is claimed is:

1. A pharmaceutical composition comprising a substantially homogeneous mixture of modafinil particles, wherein at least about 95% of the cumulative total of modafinil particles in said composition have a diameter of less than about 200 microns (μm).

2. The composition of claim 1 wherein said particles have a median diameter range of between about 2μm and about 60 μm.

3. The composition of claim 1, wherein said composition comprises between about 50 milligrams and about 700 milligrams of said modafinil.

4. A method of altering the somnolent state of a mammal, said method comprising administering an effective amount of the composition of claim 1 to said mammal.

5. The method of claim 4, wherein said somnolent state is narcolepsy.

6. The method of claim 4, wherein said effective amount comprises between about 50 milligrams/day and about 700 milligrams/day of said composition.

\* \* \* \* \*